United States Patent [19]

Rohe et al.

[11] Patent Number: 5,120,973
[45] Date of Patent: Jun. 9, 1992

[54] METHOD AND DEVICE FOR INSERTING A RADIOACTIVE RADIATION SOURCE INTO AN APPLICATOR AND WITHDRAWING IT THEREFROM

[75] Inventors: Karl-Heinz Rohe, Haan; Karl Weinlich, Wuppertal; Ulrich Bormann, Essen-Heisingen; Rainer Link, Kerpen, all of Fed. Rep. of Germany

[73] Assignee: Isotopen-Technik Dr. Sauerwein GmbH, Haan, Fed. Rep. of Germany

[21] Appl. No.: 694,425

[22] Filed: May 1, 1991

[30] Foreign Application Priority Data

Sep. 8, 1990 [DE] Fed. Rep. of Germany ...... 4028625

[51] Int. Cl.⁵ .............................. G21G 4/08
[52] U.S. Cl. .................... 250/497.1; 600/3; 600/7; 976/DIG. 353
[58] Field of Search ......... 250/497.1, 496.1; 600/7, 3; 976/DIG. 353

[56] References Cited

U.S. PATENT DOCUMENTS 4,881,937 11/1989 van't Hooft et al. ............ 600/3
4,969,863 11/1990 van't Hooft et al. ............ 600/3

FOREIGN PATENT DOCUMENTS 3313857 10/1984 Fed. Rep. of Germany ...... 600/7

*Primary Examiner*—Jack I. Berman
*Attorney, Agent, or Firm*—Toren, McGeady & Associates

[57] ABSTRACT

A method and device for inserting radioactive radiation sources into applicators and for withdrawing the radiation source and depositing them in at least one shielded loading and/or storage station. To remove a radiation source from the loading and/or storage station a traction wire with a coupling effective in the direction of traction is advanced via a fork and a switch into the loading and/or storage station, coupled with the radiation source and withdrawn as far as a stop where it is uncoupled and the traction wire is withdrawn through the fork. To introduce the radiation source into the applicator, on the other hand, a thrust wire having a coupling effective only in the direction of thrust is brought via the fork up to the radiation source and, carrying the radiation source with it, is advanced via the switch into the applicator and withdrawn again leaving the source in the applicator.

9 Claims, 5 Drawing Sheets

METHOD AND DEVICE FOR INSERTING A RADIOACTIVE RADIATION SOURCE INTO AN APPLICATOR AND WITHDRAWING IT THEREFROM

TECHNICAL FIELD OF THE INVENTION

The invention relates to a method and device for inserting radioactive radiation sources into applicators and for withdrawing the radiation sources, comprising at least one shielded loading and/or storage station for the radiation sources, and a flexible thrust wire guided in a channel and having a coupling adapted to release the radiation source in the radiation position.

BACKGROUND OF THE INVENTION AND PRIOR ART

A device of this kind is described in European published application No. 0 158 630. It consists of one or more identical modules each comprising a shielded loading and/or storage station for radiation sources, which may not be identical, and a push rod, and offers the possibility of separating the conveying device from a hollow needle in the radiation position by operating a coupling between the radiation source and the push rod that is releasable in the radiation position. The radiation source can be introduced into the hollow needle by the push rod under remote control, and is released and deposited therein. During the treatment the hollow needle can be separated from the push rod so as to give the patient a large measure of freedom of movement. At the end of the treatment the conveying device is again coupled with the hollow needle, so that after engagement of the coupling the individual radiation sources can again be withdrawn individually into the loading and/or storage station.

This known device has the disadvantage that a module with a conveying device is required for each radiation source. A further and more serious disadvantage is that in order to leave a radiation source in an applicator the coupling has to be released within the applicator. However, since the space available in hollow radiation needles for interstitial use is very limited, it is difficult to arrange a reliable release mechanism for the coupling in the radiation needle.

OBJECT OF THE INVENTION

It is therefore an object of the invention to provide a device and a process by means of which it is possible to bring radiation sources from a loading and/or storage station into an applicator, separate them there from the conveying device, leave them there for the duration of the treatment of a patient, and withdraw them again at the end of the treatment by means of the conveying device without operating or controlling the coupling in the region of the applicator. The means for doing this should be of simple construction and easy to use.

SUMMARY OF THE INVENTION

To this end, the invention consists in providing, in a device of the kind mentioned above, two drives connected respectively to a thrust and a traction wire each guided in a channel, the channels being combined at a fork. In cooperation with a radiation source the traction wire has a releasable coupling effective in the direction of traction and the thrust wire has a releasable coupling effective only in the direction of thrust. A switch is located between the channels leading to the applicators and those leading to the loading and/or storage station on the one hand and the fork on the other hand, and a means for releasing the coupling effective in the direction of traction is located between the switch and the fork.

The switch may have a plurality of entrances and exits. The entrances may be connected via channels to the loading and/or storage station and the exits via channels to a corresponding number of applicators. In order to extract a radiation source from a storage channel in the loading and/or storage station and introduce it into one of the applicators, the traction cable having a releasable coupling effective in the direction of traction is first of all advanced by means of one of the two drives via the fork and the appropriately set switch into a storage channel of the loading and/or storage station, is coupled with the radiation source, and withdraws it into the region of the release means for the coupling effective in the direction of traction, which is arranged between the fork and the switch. There, the radiation source and the traction wire are separated, the traction wire is again withdrawn to its end position, and the thrust wire is advanced through the fork until it reaches the radiation source: it then pushes the radiation source through the switch into the applicator. Since there is no connection effective in the direction of traction between this thrust wire and the radiation source, the thrust wire merely serves to move the radiation source forward by pushing and can be withdrawn to its starting position after bringing the radiation source into the applicator, leaving the radiation source in the applicator.

It will thus be seen that with two drives, one of which moves the radiation source in the direction of traction and the other in the direction of thrust, and by the provision of a fork and a switch, a very large number of radiation sources can be brought from a loading and/or storage station to a corresponding number of applicators. The applicators can then be separated from the device and remain in the patient. The device does not have to be recoupled with the applicators until the treatment is finished, when the radiation sources are moved successively back to the loading and/or storage station in the manner described.

The radiation sources can comprise needle-shaped holders that are filled with radioactive material and have at one end a sleeve with inwardly-facing spring elements which, together with a pin that is located on one end of the traction wire and can be introduced into the sleeve, forms the releasable coupling effective in the direction of traction.

Once introduced into the sleeve the pin is held frictionally by the ends of the springs and can be separated in a simple manner by means of a stop cooperating with an end face of the sleeve. For this purpose the greatest diameter of the end of the traction wire with the pin may be less than the diameter of the sleeve, and the stop may consist of a wire duct having an internal diameter greater than the diameter of the end of the traction wire carrying the pin but less than the diameter of the sleeve.

Alternatively the radiation sources may consist of needle-shaped holders that are filled with radioactive material and have at one end a sleeve with inwardly-facing resilient hooks which, together with a locking groove on a pin located at one end of the traction wire to engage with the hooks, forms the releasable coupling effective in the direction of traction. In this case a form-locking connection is formed between the hooks and the groove in the pin which cannot come apart as the radiation source is transported through the channels. In this case the means of releasing the coupling effective in the direction of traction may comprise wedge-shaped faces that engage under oblique faces on the hooks, with the greatest diameter of the end of the traction wire carrying the pin being less than the diameter of the sleeve and the internal diameter of a wire duct through the release means being greater than the diameter of the end of the traction wire carrying the pin but less than the diameter of the sleeve.

As another possibility, the radiation sources may consist of needle-shaped holders that are filled with radioactive material and consist at one end of magnetic material which, together with an extension, also of magnetic material, at one end of the traction wire, forms the releasable coupling effective in the direction of traction. In this case the release means can also consist of a stop cooperating with an end face of the sleeve, as described above for the first embodiment.

BRIEF DESCRIPTION OF THE DRAWINGS

The invention will now be described in more detail, by way of example, with reference to several embodiments shown in the drawings, in which.

DETAILED DESCRIPTION OF PREFERRED EMBODIMENTS OF THE INVENTION

Figure 1:
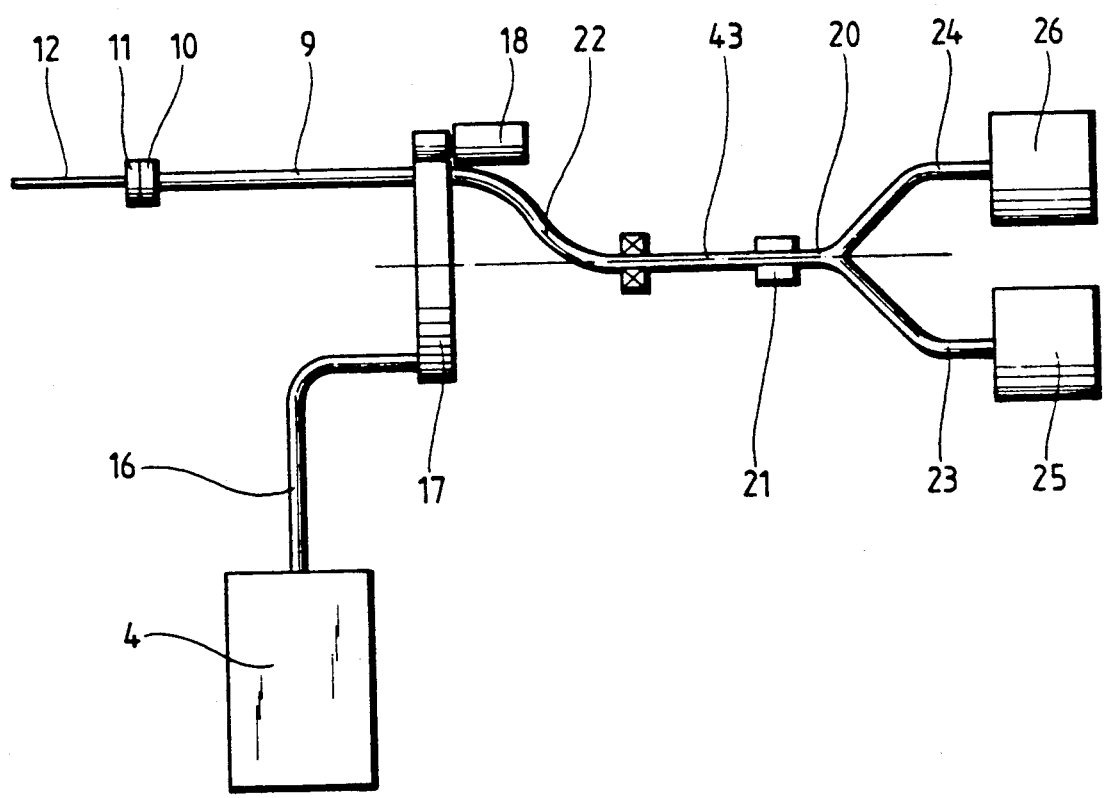
FIG. 1 shows diagrammatically a device according to the invention.

In its simplest form the device according to the invention consists of a shielded loading and/or storage container 4 for radiation sources, which are not shown in detail. This container 4 is connected via a channel 16 with a switch 17 that can be operated by a drive motor 18. A switch of this kind is described in more detail in European Patent No. 0 128 300. From the switch 17 a further channel 9 leads via a coupling 10 and a connection plate 11 to an applicator 12. The side of the switch 17 remote from the channels 9 and 16 is connected, via a rotatable channel 22, a short channel section 43 and a release means 21, to a fork 20, the channels 23, 24 of which lead to respective drives 25, 26. Such drives are described in more detail, for example in German patent specification 33 35 438. By means of the drives 25, 26 thrust and traction wires (not shown)can be passed through the channels 23, 24, 43 and the rotatable channel 22 either via the channel 16 into the loading and/or storage holder 4 or via the channel 9 to an applicator 12.

Figure 2:
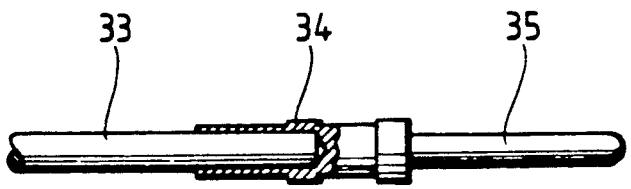
FIG. 2 is a view, partially in section, of an end of a traction wire with a coupling part effective in the direction of traction.
Figure 4:
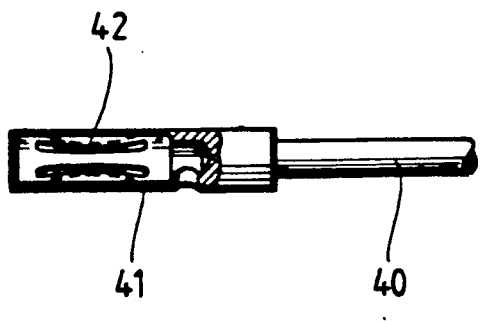
FIG. 4 shows the end of a needle-shaped holder with a coupling effective in the direction of thrust, partly in section.

As shown in FIG. 2, the traction wire 33 moved by the drive 25 has at its end a bush 34 of slightly greater diameter than the traction wire 33 and continues as a pin 35 of smaller diameter. A needle-shaped holder 40 (FIG. 4) filled with radioactive material forms the radiation source that is to be brought from the loading and/or storage container 4 and inserted into the applicator 12. At the end of the needle-shaped holder 40 there is a sleeve 41 with inwardly-facing spring elements 42. The external diameter of the pin 35 is adapted to the internal diameter of the sleeve 41 so that on pushing the pin 35 into the sleeve 41 a clamping connection is formed.

Figure 3:
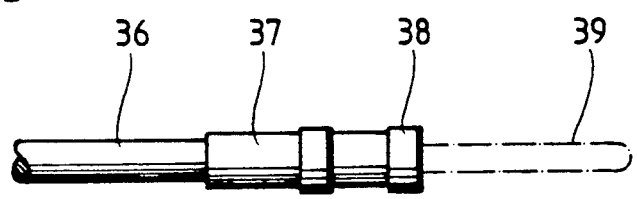
FIG. 3 shows an end of a thrust wire with coupling effective only in the direction of thrust.

If the traction wire 33 is now advanced into the loading and/or storage container 4 by means of the drive 25, with the switch 17 appropriately set, the pin is pushed into the sleeve 41, since the needle-shaped holder 40 is in its end position. If the drive 25 is operated in the opposite direction the needle-shaped holder 40 can be withdrawn by means of the traction wire 33 until it reaches the release means 21. The release means 21 consists in its simplest form of a constriction before the fork 20 through which the cable 33 with the bush 34 and the pin 35 can pass, while the diameter of the sleeve 41 is so great that it strikes against the release 21. At this point the needle-shaped holder 40 is therefore caused to separate from the traction wire 33. The drive 26 is then switched on and the appropriate thrust wire 36(FIG. 3) pushes against the sleeve 41 with its bush 37 and a cylindrical extension 38. In the same way, the cylindrical extension 38 can carry a pin 39 with a diameter small enough for it not to be gripped by the inwardly-facing spring elements 42 of the sleeve 41 so as to avoid a coupling efffective in the direction of traction being reformed. By means of the thrust wire 36 the needle-shaped holder 40 can be moved into the applicator 12 after changing over the switch 17 with the rotatable channel 22. If the thrust wire 36 is now moved back into the starting position, the needle-shaped holder 40 remains in the applicator 12, so that the applicator coupling 10 can be released without difficulty, thus giving the patient with the applicator 12 considerably more freedom of movement.

Figure 5:
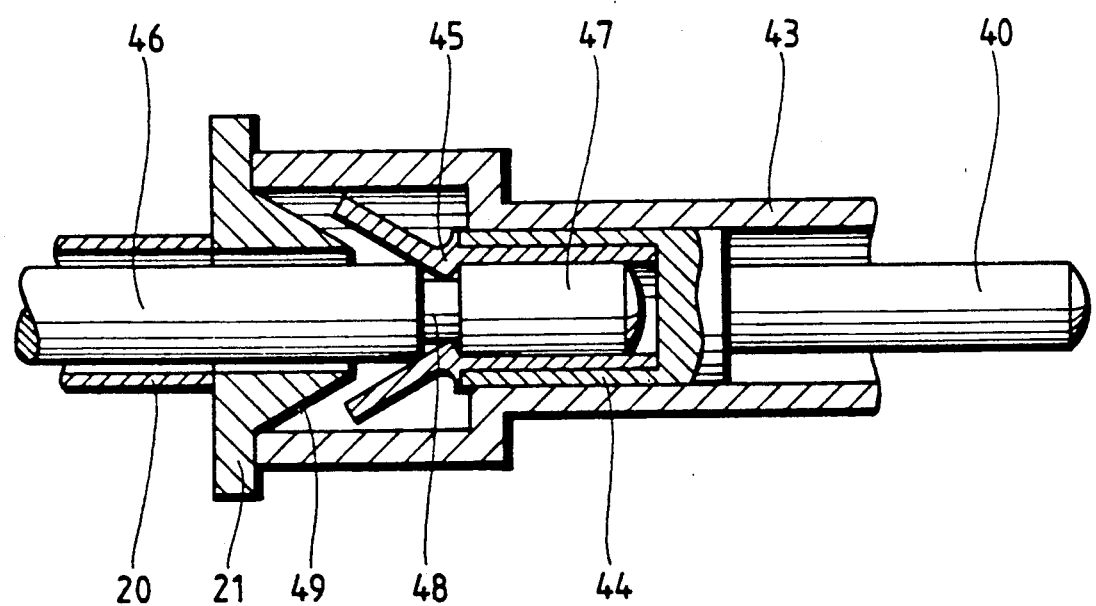
FIG. 5 shows another coupling effective in the direction of traction, with a corresponding release means.

In FIG. 5 a form-locking coupling, effective in the direction of traction, is shown together with the associated release means 21. In this case the needle-shaped holder 40 has a slit sleeve 44, with resilient hooks 45 arranged in the slits. The resilient hooks cooperate with a locking groove 48 in a pin 47 at the end of a traction wire 46. FIG. 5 shows that the pin 47 can be pushed into the sleeve 44 between the resilient hooks 45, but after engagement of the resilient hooks 45 in the groove 48 is firmly connected to the traction wire 46 in the direction of traction. To release the needle-shaped holder 40 from the traction wire 46 the traction wire 46 is withdrawn far enough for oblique faces on the resilient hooks 45 reach the region of wedge surfaces 49 on the release 21. The resilient hooks 45 are thereby opened out and come out of the groove 48, and the traction wire can be released from the needle-shaped holder 40. A channel 43 on the release 21 provides sufficient space for the resilient hooks 45 to move apart in the region of the release 21, but elsewhere ensures precise guidance of the needle-shaped holder 40.

Figure 6:
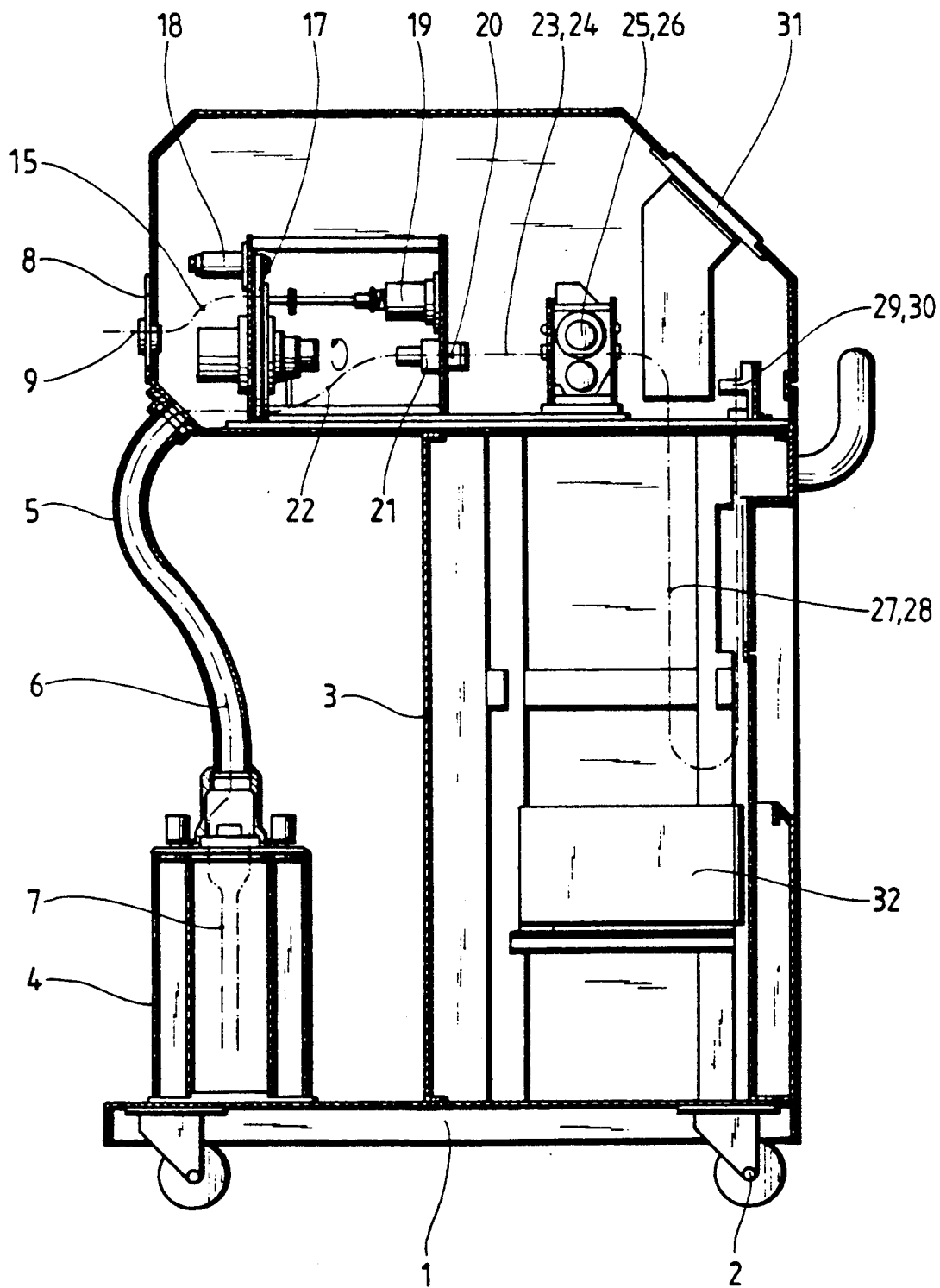
FIG. 6 shows a sectional side view of a device according to the invention.
Figure 7:
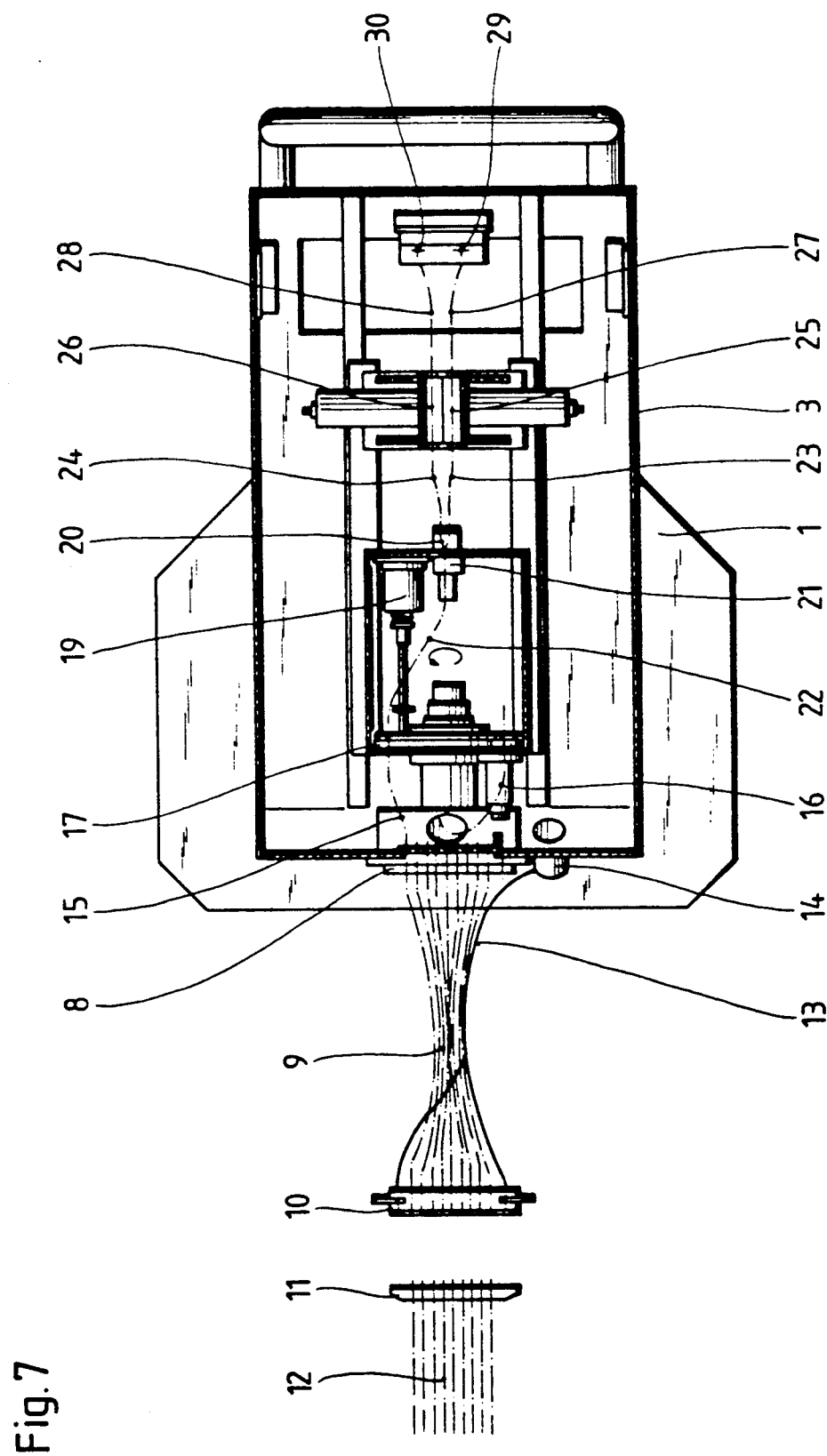
FIG. 7 shows a horizontal section through the device of FIG. 6.

FIGS. 6 and 7 illustrate the device according to the invention in detail. A housing 3 is mounted on a carriage 1 with rollers 2, leaving room on the carriage 1 for a shielded loading and/or storage container 4. The loading and/or storage container 4 is connected to the housing 34 through a tube 5. The loading and/or storage container 4 may, for example, have 16 storage channels 7 for radiation sources in the form of the needle-shaped holders 40 shown in FIG. 4. Inside the tube 5 are sixteen corresponding wire channels 6 running to the switch 17. From the same side of the switch 17 channels 15 lead to a connection plate 8, likewise for sixteen wire channels 9. These wire channels 9 end in the applicator coupling 10 which can be coupled to the connection plate 11 for the applicator channels. Sixteen applicators 12 in the form of needles are connected to this connection plate 11.

The coupling 10 includes optical means for monitoring proper connection of the connection plate 11 with the coupling 10, in the form of an optical fibre 13 which runs from the coupling 10 to an optical fibre connection 14. This prevents thrust or traction wires and/or radiation sources from being moved out of the coupling 10 when this is not connected with the connection plate 11.

In order to position the rotatable channels 22 precisely on the switch 17 for the connections for the channels 6 and 15, a catch 19 engages in the switch 17 in each position to which it is moved. Before each rotation of the switch, a test is carried out by means of a mechanical probe to ensure that there is no wire or radiation container in the switch.

Since the wire channels to the patient being treated can be from one to three meters long, the thrust or traction wires moved by the drives 25, 26 must also be correspondingly long, so storage channels 27, 28 are provided on the back of the drives 25, 26 into which the thrust or traction wires can be passed until they come up against limit switches 29, 30 that switch off the drives 25, 26.

The device is constructed in the form of a desk and has a front plate 31 carrying LCD indicators and buttons. A container 32 with an accumulator and an electronic control unit are housed in the lower part of the housing 3.

By means of the device according to the invention radiation sources can be inserted into and withdrawn from applicators in a programmed manner, without the operators being exposed to radioactive radiation.

What is claimed is:

1. A device for inserting and withdrawing radioactive radiation sources into and from applicators, comprising at least one shielded loading and/or storage station for the radiation sources and a flexible thrust wire that is guided in a channel and has a coupling that releases said radiation sources in the radiation position, said device also comprising: two drives connected respectively with a thrust and a traction wire each guided in a channel, said channels being combined in a fork, said traction wire cooperating with a radiation source in a releasable coupling effective in the direction of traction and said thrust wire cooperating with a radiation source in a releasable coupling effective only in the direction of thrust; a switch located between the channels leading to the applicators and those leading to the loading and/or storage station on the one side and the fork on the other side; and a release means for the coupling effective in the direction of traction located between the switch and the fork.

2. A device according to claim 1 wherein the radiation sources consist of needle-shaped holders that are filled with radioactive material and have at one end a sleeve having inwardly-facing spring elements which, together with a pin that can be inserted in the sleeve and has a diameter such that it cooperates with the ends of the springs, forms the releasable coupling effective in the direction of traction.

3. A device according to claim 2, wherein the release means for the coupling effective in the direction of traction comprises a stop that cooperates with an end face of the sleeve.

4. A device according to claim 3, wherein the greatest diameter of the end of the traction wire with the pin is smaller than the diameter of the sleeve and the stop consists of a duct for the wire having an internal diameter greater than the diameter of the end of the traction wire with the pin but smaller than the diameter of the sleeve.

5. A device according to claim 1, wherein the radiation sources consist of needle-shaped holders that are filled with radioactive material and have on one end a sleeve having resilient, inwardly-directed hooks which, together with a pin located at one end of the traction wire and having a locking groove to engage the hooks, forms the releasable coupling effective in the direction of traction.

6. A device according to claim 5 wherein the release means for the coupling effective in the direction of traction comprises wedge faces that engage under oblique faces on the hooks, the greatest diameter of the end of the traction wire with the pin is smaller than the diameter of the sleeve, and the internal diameter of a wire duct through the release means is greater than the diameter of the end of the traction cable with the faces but smaller than the sleeve diameter.

7. A device according to claim 1, wherein the radiation sources consist of needle-shaped holders that are filled with radioactive materials and of which one end consists of a magnetic material that, together with an extension made of magnetic material on one end of the traction wire, forms the releasable coupling effective in the direction of traction.

8. A device according to claim 7, wherein the release means for the coupling effective in the direction of fraction consists of a stop that cooperates with an end face of the end of the holder.

9. A device for inserting and removing radioactive radiation sources into and from applicators wherein said sources can be transported between a loading and/or storage station by means of flexible wires coupled to said sources and guided through channels, said device comprising first and second drives respectively for a traction and a thrust wire, channels for said traction and thrust wires leading from said drives and combining in a fork into a common channel switchably connectable by a switching means to channels leading respectively to at least one shielded loading and/or storage container and to said applicators, said traction wire cooperating with a radiation source in a releasable coupling effective in the direction of traction and said thrust wire cooperating with a radiation source in a releasable coupling effective only in the direction of thrust, and means for releasing said coupling effective in the direction of traction located between said switching means and said fork.

* * * * *